(12) United States Patent
Kuruma et al.

(10) Patent No.: US 7,602,495 B2
(45) Date of Patent: Oct. 13, 2009

(54) METHOD FOR MEASURING DISSOCIATION CONSTANT BY SURFACE PLASMON RESONANCE ANALYSIS

(75) Inventors: Koji Kuruma, Kanagawa (JP); Hirohiko Tsuzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/660,958

(22) PCT Filed: Aug. 24, 2005

(86) PCT No.: PCT/JP2005/015318

§ 371 (c)(1),
(2), (4) Date: Oct. 4, 2007

(87) PCT Pub. No.: WO2006/022277

PCT Pub. Date: Mar. 2, 2006

(65) Prior Publication Data

US 2008/0037023 A1    Feb. 14, 2008

(30) Foreign Application Priority Data

Aug. 24, 2004    (JP) ............................. 2004-244151

(51) Int. Cl.
*G01N 21/55* (2006.01)
(52) U.S. Cl. .................................................... 356/445
(58) Field of Classification Search ................ 356/445, 356/419, 128; 435/69.52, 320.1, 7.1; 250/227.16
See application file for complete search history.

(56) References Cited

U.S. PATENT DOCUMENTS 5,861,254 A    1/1999    Schneider et al.

(Continued)

FOREIGN PATENT DOCUMENTS

EP    1 243 916 A3    9/2002

(Continued)

OTHER PUBLICATIONS

Iva Navratilova and David G. Myszka, Investigating Biomolecular Interactions and Binding Properties Using SPR Biosensors, pp. 158-161, from "Surface Plasmon Resonance Based Sensors", Springer-Verlag Berlin Heidelberg, ISBN: 3-540-33918-3 (2006).

(Continued)

*Primary Examiner*—Tarifur R. Chowdhury
*Assistant Examiner*—Isiaka O Akanbi
(74) *Attorney, Agent, or Firm*—Sughrue Mion, PLLC (57) ABSTRACT

An object to be solved by the present invention is to determine the dissociation constant of an analyte molecule immobilized on a metal surface and a molecule that interacts therewith in surface plasmon resonance (SPR) analysis via an analytical method that produces a low noise level (i.e., a noise width of a reference chip), small baseline fluctuations (i.e., signal changes of a reference chip), and highly reliable results of measurement. The present invention provides a method for determining a dissociation constant of an analyte molecule immobilized on a metal surface and a molecule that interacts therewith, wherein changes in surface plasmon resonance signals are measured by using a surface plasmon resonance measurement device comprising a flow channel system having a cell formed on a metal film and a light-detecting means for detecting the state of surface plasmon resonance by measuring the intensity of a light beam totally reflected on the metal film; wherein a change in surface plasmon resonance signals is measured in a state where the flow of the liquid has been stopped, after the liquid contained in the above flow channel system has been exchanged; and wherein the dissociation constant is determined based on the results of measurement of signal changes.

11 Claims, 2 Drawing Sheets

U.S. PATENT DOCUMENTS

| | | | |
|---|---|---|---|
| 6,156,493 | A | 12/2000 | Stayton |
| 6,462,809 | B1 * | 10/2002 | Ryan et al. .................. 356/128 |
| 6,480,282 | B1 | 11/2002 | Chinowsky et al. |
| 6,713,610 | B1 | 3/2004 | Kucherlapati et al. |
| 7,057,732 | B2 * | 6/2006 | Jorgenson et al. ........... 356/445 |
| 2002/0156008 | A1 * | 10/2002 | Kaumaya et al. .............. 514/12 |
| 2002/0177161 | A1 | 11/2002 | Latov et al. |
| 2003/0235890 | A1 * | 12/2003 | Wyllie et al. ............. 435/69.52 |
| 2004/0072375 | A1 | 4/2004 | Gjerde et al. |
| 2005/0146723 | A1 | 7/2005 | Kuruma et al. |
| 2006/0087656 | A1 * | 4/2006 | Barford et al. .............. 356/445 |
| 2006/0209305 | A1 | 9/2006 | Kuruma et al. |
| 2006/0227328 | A1 * | 10/2006 | Vanwiggeren et al. ...... 356/445 |

FOREIGN PATENT DOCUMENTS

| | | |
|---|---|---|
| JP | 4-501462 A | 3/1992 |
| JP | 6-501546 A | 2/1994 |
| JP | 09-257806 A | 3/1997 |
| JP | 10-38797 A | 2/1998 |
| JP | 10-267841 A | 10/1998 |
| JP | 11-512186 A | 10/1999 |
| JP | 2000-065731 A | 3/2000 |
| JP | 2000-65731 A | 3/2000 |
| JP | 2001-255267 A | 9/2001 |
| JP | 2002-131319 A | 5/2002 |
| JP | 2002-357544 A | 12/2002 |
| JP | 2003-194820 A | 7/2003 |
| JP | 2003-527580 A | 9/2003 |
| JP | 2003-302399 A | 10/2003 |
| JP | 2003-329579 A | 11/2003 |
| WO | WO 92/01217 | 1/1992 |
| WO | 99/61896 A | 12/1999 |
| WO | 01/69207 A1 | 9/2001 |

OTHER PUBLICATIONS

Bother B et al., "Defining the molecular basis of Arf and Hdm2 interactions". Journal of Molecular Biology, London, GB, vol. 314, No. 2, Nov. 23, 2001, pp. 263-277.

European Search Report dated Mar. 1, 2005.

K. H. Pearce et al., Biochemistry, 38, 1999, pp. 81-89.

* cited by examiner

METHOD FOR MEASURING DISSOCIATION CONSTANT BY SURFACE PLASMON RESONANCE ANALYSIS

TECHNICAL FIELD

The present invention relates to a method for measuring the dissociation constant of an analyte molecule immobilized on a metal surface and a molecule that interacts therewith by surface plasmon resonance (SPR) analysis.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. An example of a surface plasmon resonance measurement device is the device described in Japanese Patent Laid-Open (Kokai) No. 2001-330560.

When a specific binding reaction between a physiologically active substance and a test substance is measured, the binding reaction is generally measured by: connecting in series a reference cell, to which a physiologically active substance interacting with a test substance does not bind, with a detection cell, to which a physiologically active substance interacting with a test substance binds; placing the connected cells in a flow channel system; and feeding a liquid through the reference cell and the detection cell, so as to carry out the measurement of the binding reaction. During the measurement, the liquid contained in the above flow channel system is exchanged from a reference liquid containing no test substance to be measured to a sample liquid containing a test substance to be measured, so as to cause the binding reaction between the physiologically active substance and the test substance to be initiated, and to measure a change in signals due to a lapse of time.

As mentioned above, a biosensor that uses SPR detects the binding of an analyte to a sensor (a metal film and a ligand) as a change in the refractive index (and an angular change of a dark line caused thereupon). If the time is plotted on the horizontal axis and the binding signal is plotted on the vertical axis, a signal (the amount of binding or the like) that is referred to as a so-called "sensorgram" can be observed with the elapse of time. It is important to carry out fitting of the following rate equation (i) to the sensorgram followed by determination of the rate coefficients such as the adsorption rate coefficient (ka) and the dissociation rate coefficient (kd).

$$dR/dt = ka \times C \times \{Rmax - R(t)\} - kd \times R(t) \qquad (i)$$

$R(t) = (ka \times C \times Rmax)/(ka \times C + kd) \times (1 - \exp(-ka \times C + kd) \times t))$ (ii) (the result of solving equation (i))

wherein ka represents an adsorption rate coefficient; kd represents a dissociation rate coefficient; C represents an analyte concentration (known); Rmax represents the theoretical maximum amount of binding; and t represents a time.

DISCLOSURE OF THE INVENTION

Object to be Solved by the Invention

According to the aforementioned method for measuring signal changes with the elapse of time, wherein the liquid contained in the above flow channel system is exchanged from a reference liquid containing no test substance to be measured to a sample liquid containing a test substance to be measured, so as to cause the binding reaction between the physiologically active substance and the test substance to be initiated, and to measure a change in signals due to a lapse of time, a noise width and baseline fluctuations of signal changes of a reference cell within a measurement time were problematic, and it was difficult to attain highly reliable data for the binding detection. As a means for dissolving such drawback, JP Patent Application No. 2003-404040 discloses a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein the above method is characterized in that a change in surface plasmon resonance is measured in a state where the flow of the liquid has been stopped, after the liquid contained in the above flow channel system has been exchanged. By measuring changes in surface plasmon resonance in a state where the flow of the liquid has been stopped, after the liquid contained in the above flow channel system has been exchanged, highly reliable results of measurement with a low noise level (i.e., a noise width of a reference chip) and small baseline fluctuations (i.e., signal changes of a reference chip) can be attained. However, there has been no report concerning the measurement of rate coefficients such as ka (an adsorption rate coefficient) and kd (a dissociation rate coefficient) based on the results of measurement of changes in SPR signals obtained by the method of measuring signal changes in a state where the flow of the liquid has been stopped, after the liquid contained in the flow channel system of the surface plasmon resonance measurement device has been exchanged. Accordingly, an object to be solved by the present invention is to determine the dissociation constant of an analyte molecule immobilized on a metal surface and a molecule that interacts therewith in surface plasmon resonance (SPR) analysis via an analytical method that produces a low noise level (i.e., a noise width of a reference chip), small baseline fluctuations (i.e., signal changes of a reference chip), and highly reliable results of measurement.

Means for Solving the Object

The present inventors have demonstrated for the first time that rate coefficients such as ka (an adsorption rate coefficient) and kd (a dissociation rate coefficient) could be accurately determined based on the results of measurement of signal changes obtained by the method for measuring SPR signal changes in a state where the flow of the liquid has been stopped, after the liquid contained in the flow channel system of the surface plasmon resonance measurement device has been exchanged. This has led to the completion of the present invention.

Thus, the present invention provides a method for determining a dissociation constant of an analyte molecule immobilized on a metal surface and a molecule that interacts therewith, wherein changes in surface plasmon resonance signals are measured by using a surface plasmon resonance measurement device comprising a flow channel system having a cell formed on a metal film and a light-detecting means for detecting the state of surface plasmon resonance by measuring the intensity of a light beam totally reflected on the metal film; wherein a change in surface plasmon resonance signals is measured in a state where the flow of the liquid has been stopped, after the liquid contained in the above flow channel system has been exchanged; and wherein the dissociation constant is determined based on the results of measurement of signal changes.

Preferably, an adsorption rate coefficient (ka) and a dissociation rate coefficient (kd) are determined based on the results of measurement of changes in surface plasmon resonance signals, and a dissociation constant (KD) is determined using an equation represented by KD=kd/ka based on the determined adsorption rate coefficient (ka) and the dissociation rate coefficient (kd).

Preferably, an adsorption rate coefficient (ka) and a dissociation rate coefficient (kd) are determined based on the results of measurement of changes in surface plasmon resonance signals by using the following equations (1), (2), and (3):

$$d\theta/dt = ka \times c_s \times (1-\theta) - kd \times \theta \quad (1)$$

wherein $\theta$ represents an adsorption ratio (=amount of adsorption/amount of saturated adsorption); ka represents an adsorption rate coefficient; kd represents a dissociation rate coefficient; and $c_s$ represents the concentration of the analyte molecule that exists near the metal surface;

$$\partial c/\partial t = D \times \partial^2 c/\partial x^2 \quad (2)$$

wherein x represents a distance from a metal surface; D represents a diffusion coefficient of the analyte molecule; and c represents the concentration of the analyte molecule, provided that when x is 0, c is $c_s$; and $$\theta = R/R\text{max} \quad (3)$$

wherein $\theta$ represents an adsorption ratio (=amount of adsorption/amount of saturated adsorption); R represents a surface plasmon signal; and Rmax represents a signal resulting when an analyte molecule is saturatedly adsorbed.

Preferably, the dissociation constant is determined while making corrections based on the supposition that the time required for the liquid exchange is an adsorption phenomenon under ideal conditions.

Preferably, the dissociation constant is determined by using nonlinear regression analysis.

Preferably, a surface plasmon resonance measurement device is used, which comprises a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, a flow channel system comprising a cell formed on the above metal film, and a light-detecting means for detecting the state of surface plasmon resonance by measuring the intensity of the light beam totally reflected at the above interface.

Preferably, the liquid contained in the above flow channel system is exchanged from a reference liquid containing no test substance to be measured to a sample liquid containing a test substance to be measured, and thereafter, a change in surface plasmon resonance is measured in a state where the flow of the sample liquid has been stopped.

Preferably, a reference cell, to which a physiologically active substance interacting with a test substance does not bind, is connected in series with a detection cell, to which a physiologically active substance interacting with a test substance binds, the connected cells are placed in a flow channel system, and a liquid is then fed through the reference cell and the detection cell.

Preferably, the ratio (Ve/Vs) of the amount of a liquid exchanged (Ve ml) in a single measurement to the volume of the above cell (Vs ml) is between 1 and 100. More preferably, the ratio (Ve/Vs) is between 1 and 50.

Preferably, the time required for the exchange of the liquid contained in the above flow channel system is between 0.01 second and 100 seconds.

BEST MODES FOR CARRYING OUT THE INVENTION

Hereafter, embodiments of the invention will be described.

The present invention relates to a method for measuring dissociation constants of an analyte molecule immobilized on a metal surface and a molecule that interacts therewith. In the method for measuring dissociation constants according to the present invention, more specifically, changes in surface plasmon resonance signals are measured by using a surface plasmon resonance measurement device comprising a flow channel system having a cell formed on a metal film and a light-detecting means for detecting the state of surface plasmon resonance by measuring the intensity of a light beam totally reflected on the metal film, wherein a change in surface plasmon resonance signals is measured in a state where the flow of the liquid has been stopped, after the liquid contained in the above flow channel system has been exchanged, and wherein the dissociation constant is determined based on the results of measurement of signal changes.

Another aspect of the present invention provides a method for measuring changes in surface plasmon resonance signals which comprises determining the dissociation constant between an analyte molecule immobilized on a metal surface and a molecule that interacts therewith based on the results of measurement of changes of surface plasmon resonance signals by using a surface plasmon resonance measurement device comprising a flow channel system having a cell formed on a metal film and a light-detecting means for detecting the state of surface plasmon resonance by measuring the intensity of a light beam totally reflected on the metal film, wherein a change in surface plasmon resonance signals is measured in a state where the flow of the liquid has been stopped, after the liquid contained in the above flow channel system has been exchanged.

The analyte molecule adsorbs to a molecule that interacts therewith immobilized on the surface of the metal with the elapse of time. This phenomenon can be represented by the following equation (1):

$$d\theta/dt = ka \times c_s \times (1-\theta) - kd \times \theta \qquad (1)$$

wherein θ represents an adsorption ratio (=amount of adsorption/amount of saturated adsorption); ka represents an adsorption rate coefficient; kd represents a dissociation rate coefficient; and $c_s$ represents the concentration of the analyte molecule that exists near the metal surface.

Under ideal conditions where a liquid on a metal surface can be constantly replaced with a fresh liquid, $c_s$ is maintained at a constant level, and ka and kd can be determined based on the assay results by solving simple difference equations.

However, a liquid flow on the metal surface is very slow, and a solution containing analyte molecules must be flowed rapidly in order to maintain $c_s$ at a constant level. In contrast, surface plasmon signal is fluctuated by a disturbed liquid flow on the metal surface, and a large quantity of analyte molecules must be used in order to flow the solution rapidly. Accordingly, it is practically impossible to maintain $c_s$ at a constant level.

When $c_s$ is not maintained at a constant level, changes in the concentration resulting from adsorption/dissociation of analyte molecules are functions that are varied by offshore diffusion of analyte molecules. Such diffusion is represented by the following equation (2):

$$\partial c/\partial t = D \times \partial^2 c/\partial x^2 \qquad (2)$$

wherein x represents a distance from a metal surface; D represents a diffusion coefficient of the analyte molecule; and c represents the concentration of the analyte molecule, provided that when x is 0, c is $c_s$.

The surface plasmon signal R (a difference from the surface plasmon signal when analyte molecules are not adsorbed) is known to be proportional to the amount of analyte molecules adsorbed on the metal surface and is represented by the following equation (3):

$$\theta = R/R\max \qquad (3)$$

wherein θ represents an adsorption ratio (=amount of adsorption/amount of saturated adsorption); R represents a surface plasmon signal; and Rmax represents a signal resulting when an analyte molecule is saturatedly adsorbed.

By using the above equations (1), (2), and (3), the adsorption rate coefficient ka, the dissociation rate coefficient kd, and a ratio thereof, i.e., the equilibrium dissociation coefficient KD (=ka/kd), can be determined from the signal measured by the experiment.

Hereafter, a method of analysis is described in detail.

When the rate of replacing a reference solution that contains no analyte molecules with a sample solution that contains analyte molecules is sufficiently faster than the adsorption rate of analyte molecules and when a regular offshore flow of a solution with a concentration of $C_0$ occurs constantly (hereafter such situation is referred to as the "ideal condition"), values of interest can be obtained by solving the equation (1). More specifically, changes in surface plasmon signals are represented by equation (4):

$$dR/dt = ka \times C0 \times (R\max - R)kd \times R \qquad (4).$$

Changes in the signal R at the time point "t" obtained via experiment are subjected to nonlinear regression analysis using the equation (4). Thus, the adsorption rate coefficient ka and the dissociation rate coefficient kd can be determined. Since the Rmax value is affected by the state of analyte molecules bound to a metal surface or other conditions, it is preferable to determine ka and kd simultaneously. This requires nonlinear regression analysis with 3 unknown quantities. In order to fulfill such requirement, however, the linear velocity of a solution must be increased. This disadvantageously results in an unstabilized surface plasmon signal and an increased noise level.

When the rate of replacing a reference sample that contains no analyte molecules with a sample solution that contains analyte molecules at concentration of $C_0$ is sufficiently faster than the adsorption rate of analyte molecules and the liquid flow is stopped immediately after liquid exchange (hereafter this is referred to as the "stopped flow (SF) conditions), the adsorption rate coefficient ka and the dissociation rate coefficient kd can be determined using the equation (1), (2), or (3). Specifically, in the equations (1), (2), and (3), difference equations can be approximately replaced with the following difference equations.

$$R[t] = (ka \times C[0,(t-\Delta t)] \times (R\max - R[t-\Delta t]) - kd \times R[t-\Delta t]) \times \Delta t + R[t-\Delta t] \qquad (5)$$

$$C[0,t] = D \times (C[\Delta x,(t-\Delta t)] - C[0,(t-\Delta t)]) + C[0,(t-\Delta t)] - (ka \times C[0,(t-\Delta t)] \times (R\max - R[t-\Delta t]) - (kd \times R[t-\Delta t])/R\max \times Sm \times \Delta t)/\Delta x \qquad (6)$$

$$C[n \times \Delta x, t] = D \times (C[(n+1) \times \Delta x, (t-\Delta t)] + C[(n-1) \times \Delta x, (t-\Delta t)] - 2 \times C[\Delta x,(t-\Delta t)]) + C[\Delta x, (t-\Delta t)] \qquad (7)$$

wherein R[t] represents a surface plasmon signal at the time point t; Δt represents a minute time; C[x, t] represents a concentration of the analyte molecule at a point that is the distance x away from a metal surface at the time point t; Δx represents a minute distance; and Sm represents the amount of saturatedly adsorbed analyte molecules.

When Δx and Δt are sufficiently small, the equations (5), (6), and (7) are approximated by the equations (1), (2), and (3). In this case, diffusion of analyte molecules at the time point Δt must be sufficiently shorter than the distance Δx. More specifically, the tentative diffusion coefficient $D_M$ represented by the following equation (8) must be between 0.01 and 0.5, and it is preferably between 0.05 and 0.45.

$$\Delta x^2/D \times \Delta t = D_M \qquad (8)$$

Further, the level of changes in the concentration of analyte molecules at a point of contact with a metal surface should be sufficiently small at the time point Δt. It is represented by the equation (9):

$$(C[0,t+\Delta t] - C[0,t]) << C[0,t] \qquad (9)$$

It is necessary for Δx to fulfill the following equation (10) from equations (6), (8), or (9):

$$\Delta x << D/(D_M \times Sm \times ka) \qquad (10)$$

When the equation (10) is expressed as the following equation (11) using the degree of incidence constant Ax, Ax must be between 0.0001 and 0.1, and it is preferably between 0.001 and 0.03.

$$\Delta x = Ax \times D/(D_M \times Sm \times ka) \qquad (11)$$

When usual assay results are analyzed, calculation is performed while ka remains unknown. Accordingly, $\Delta x$ must be determined by assigning a value that is larger than the maximum value, which is deduced to be ka value.

The surface plasmon signal R[t] can be represented by applying the boundary conditions of the following equation (12) to the aforementioned equations (4) to (11).

$$C[n \times \Delta x, 0] = C_0 \quad (12)$$

Figure 3:
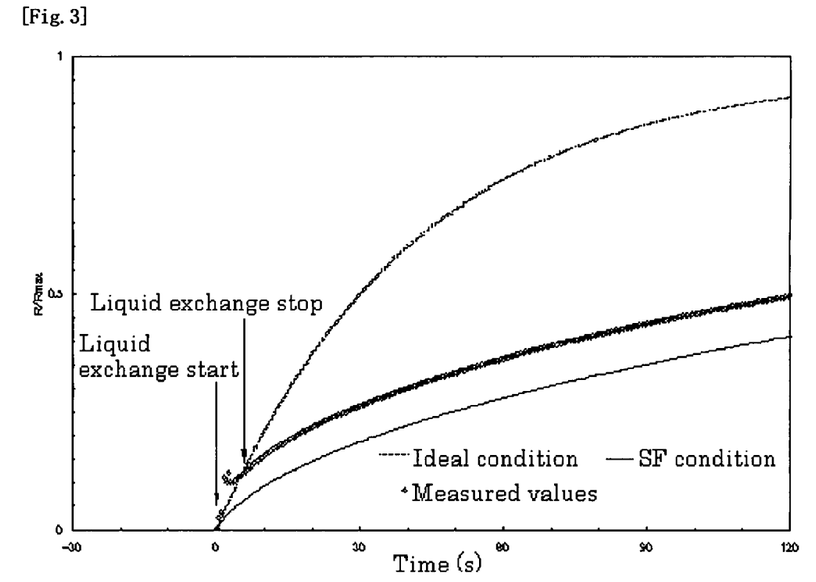
FIG. 3 shows a comparison of the SPR curve attained under the ideal conditions, that attained under the stop-flow conditions, and the measured SPR curve.

Under the SF conditions, the rate of replacing a reference solution that contains no analyte molecules with a sample solution that contains analyte molecules at a concentration $C_0$ is deduced to be sufficiently faster than the adsorption rate of analyte molecules. Such deduction is difficult to prove in an actual assay system (under real SF conditions). Accordingly, changes occur more rapidly than SF conditions upon liquid exchange, as shown in FIG. 3. Since liquid flows at a high speed at the time of liquid exchange, assay cannot be sufficiently carried out due to noises. However, adsorption is observed under ideal conditions.

In actual analysis, the following difference equation (13) is calculated based on the equation (4) during the time of liquid exchange ($0 \leq t \leq t_i$). Analysis can be carried out in accordance with the equation (14), (15), or (16) after the liquid exchange ($t_i \leq t$). Values that satisfy the requirements of equations (8) to (11) are selected for $\Delta x$ and $\Delta t$.

When the condition $0 \leq t \leq t_i$ is satisfied:

$$R[t] = (ka \times C_0 \times (Rmax - R[t - \Delta t]) - kd \times R[t - \Delta t]) \times \Delta t + R[t - \Delta t] \quad (13).$$

When the condition $t_i \leq t$ is satisfied:

$$R[t] = (ka \times C[0, (t - \Delta t)] \times (Rmax - R[t - \Delta t]) - kd \times R[t - \Delta t]) \times \Delta t + R[t - \Delta t], \quad (14)$$

$$C[0, t] = D \times (C[\Delta x, (t - \Delta t)] - C[0, (t - \Delta t)]) + C[0, (t - \Delta t)] - (ka \times C[0, (t - \Delta t)] \times (Rmax - R[t - \Delta t]) - (kd \times R[t - \Delta t]) / Rmax \times Sm \times \Delta t) / \Delta x \quad (15)$$

$$C[n \times \Delta x, t] = D \times (C[(n + 1) \times \Delta x, (t - \Delta t)] + C[(n - 1) \times \Delta x, (t - \Delta t)] - 2 \times C[\Delta x, (t - \Delta t)]) + C[\Delta x, (t - \Delta t)] \quad (16)$$

The equation (17) is employed as the boundary condition.

$$C[n \times \Delta x, t_i] = C_0 \quad (17)$$

Figure 4:
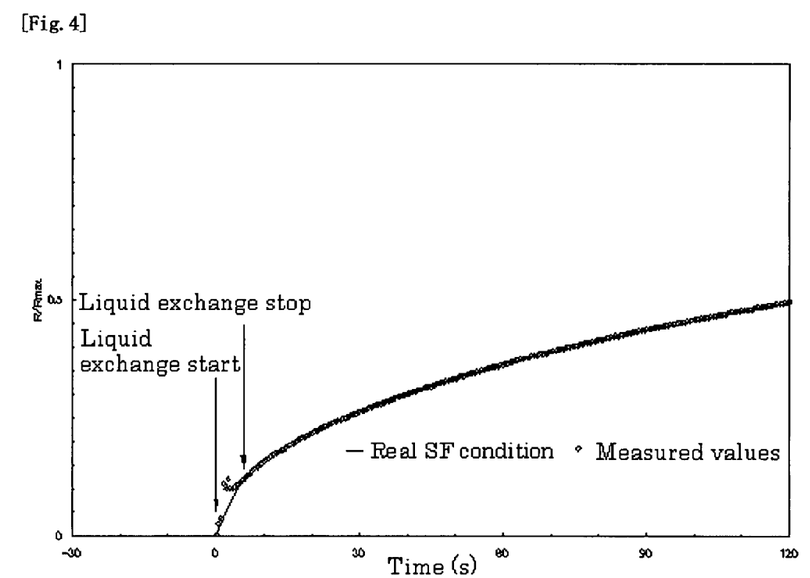
FIG. 4 shows the results of a comparison of the curves of all the regions obtained from ka, kd, Rmax, and D determined by the method of the present invention with the measured SPR curve.

In order to subject the actual assay results to nonlinear regression analysis under the real SF conditions, it is preferable to handle the diffusion coefficient D as an unknown quantity in addition to ka, kd, and Rmax. The diffusion coefficient D is considered to be determined from a molecular weight by using the Einstein's equation. In practice, influences of molecular configurations or solvents are significant, and thus it is preferable to actually perform measurement. In the $0 \leq t \leq t_i$ region, noises generated in the assay system is large, and thus, use thereof for calculation results in a larger error. Thus, nonlinear regression analysis is carried out concerning the $t_i \leq t$ region by employing ka, kd, Rmax, and D as unknown quantities. The curve indicating the entire $0 \leq t$ region obtained from the obtained ka, kd, Rmax, and D is compared with the curve indicating the measured value. These curves are adequately consistent with each other, as shown in FIG. 4.

Actual calculation may be carried out via any type of algorithm as long as any of the difference equations (13) to (17) is employed. Also, non regression analysis may be carried out via any conventional techniques.

In the present invention, the noise width of a change in signals of a reference cell during measurement and base line fluctuation can be suppressed by measuring a change in surface plasmon resonance in a state where the flow of a liquid has been stopped, so that binding detection data with high reliability can be obtained. The time of the stop of the flow of the liquid is not particularly limited. For example, it may be between 1 second and 30 minutes, preferably between 10 seconds and 20 minutes, and more preferably between 1 minute and 20 minutes.

In the present invention, preferably, the liquid contained in a flow channel system is exchanged from a reference liquid containing no test substance to be measured to a sample liquid containing a test substance to be measured, and thereafter, a change in surface plasmon resonance can be measured in a state where the flow of the sample liquid has been stopped.

In the present invention, preferably, a reference cell, to which a substance interacting with a test substance does not bind, is connected in series with a detection cell, to which a substance interacting with a test substance binds, the connected cells are placed in a flow channel system, and a liquid is then fed through the reference cell and the detection cell, so that a change in surface plasmon resonance can be measured.

In addition, in the present invention, the ratio (Ve/Vs) of the amount of a liquid exchanged (Ve ml) in a single measurement to the volume (Vs ml) of a cell used in measurement (and when the aforementioned reference cell and detection cell are used, the total volume of these cells) is preferably between 1 and 100, Ve/Vs is more preferably between 1 and 50, and particularly preferably between 1 and 20, The volume (Vs ml) of a cell used in measurement is not particularly limited. It is preferably between $1 \times 10^{-6}$ and 1.0 ml, and particularly preferably between $1 \times 10^{-5}$ and $1 \times 10^{-1}$ ml. The period of time necessary for exchanging the liquid is preferably between 0.01 second and 100 seconds, and particularly preferably between 0.1 second and 10 seconds.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light. The surface plasmon resonance measurement device used in the present invention will be described below.

The surface plasmon resonance measurement device is a device for analyzing the properties of a substance to be measured using a phenomenon whereby a surface plasmon is excited with a lightwave. The surface plasmon resonance measurement device used in the present invention comprises a dielectric block, a metal film formed on a face of the dielectric block, a light source for generating a light beam, an optical system for allowing the above light beam to enter the above dielectric block such that total reflection conditions can be obtained at the interface between the above dielectric block and the above metal film and that components at various incident angles can be contained, and a light-detecting means for detecting the state of surface plasmon resonance by measuring the intensity of the light beam totally reflected at the above interface.

Moreover, as stated above, the above dielectric block is formed as one block comprising the entity of the entrance face and exit face of the above light beam and a face on which the above metal film is formed, and the above metal film is integrated with this dielectric block.

In the present invention, more specifically, a surface plasmon resonance measurement device shown in FIGS. 1 to 32 of Japanese Patent Laid-Open No. 2001-330560, and a surface plasmon resonance device shown in FIGS. 1 to 15 of Japanese Patent Laid-Open No. 2002-296177, can be preferably used. All of the contents as disclosed in Japanese Patent Laid-Open Nos. 2001-330560 and 2002-296177 cited in the present specification are incorporated herein by reference as a part of the disclosure of this specification.

For example, the surface plasmon resonance measurement device described in Japanese Patent Laid-Open No. 2001-330560 is characterized in that it comprises: a dielectric block; a thin metal film formed on a face of the dielectric block; multiple measurement units comprising a sample-retaining mechanism for retaining a sample on the surface of the thin film; a supporting medium for supporting the multiple measurement units; a light source for generating a light beam; an optical system for allowing the above light beam to enter the dielectric block at various angles so that total reflection conditions can be obtained at the interface between the dielectric block and the metal film; a light-detecting means for measuring the intensity of the light beam totally reflected at the above interface and detecting the state of attenuated total reflection caused by surface plasmon resonance; and a driving means for making the above supporting medium, the above optical system and the above light-detecting means move relative to one another, and successively placing each of the above multiple measurement units in a certain position appropriate to the above optical system and the above light-detecting means, so that the above total reflection conditions and various incident angles can be obtained with respect to each dielectric block of the above multiple measurement units.

It is to be noted that in the above measurement device, the above optical system and light-detecting means are kept in a resting state and the above driving means makes the above supporting medium move.

In such a case, the above supporting medium is desirably a turntable for supporting the above multiple measurement units on a circle centered on a rotation axis, and the above driving means is desirably a means for intermittently rotating this turntable. In this case, a medium for supporting the above multiple measurement units that are linearly arranged in a line may be used as the above supporting medium, and a means that makes such a supporting medium move linearly in an intermittent fashion in the direction in which the above multiple measurement units are arranged may be applied as the above driving means.

Otherwise, on the contrary, it may also be possible that the above supporting medium be retained in a resting state and that the above driving means makes the above optical system and light-detecting means move.

In such a case, the above supporting medium is desirably a medium for supporting the above multiple measurement units on a circle, and the above driving means is desirably a means for intermittently rotating the above optical system and light-detecting means along the multiple measurement units supported by the above supporting medium. In this case, a medium for supporting the above multiple measurement units that are linearly arranged in a line may be used as the above supporting medium, and a means that makes the above optical system and light-detecting means move linearly in an intermittent fashion along the multiple measurement units supported by the above supporting medium may be applied as the above driving means.

Otherwise, when the above driving means has a rolling bearing that supports a rotation axis, the driving means is desirably configured such that after the rotation axis has been rotated to a certain direction and a series of measurements for the above multiple measurement units has been terminated, the above rotation axis is equivalently rotated to the opposite direction, and then it is rotated again to the same above direction for the next series of measurements.

In addition, the above-described measurement device is desirably configured such that the above multiple measurement units are connected in a line with a connecting member so as to constitute a unit connected body and that the above supporting medium supports the unit connected body.

Moreover, in the above-described measurement device, it is desirable to establish a means for automatically feeding a given sample to each sample-retaining mechanism of the multiple measurement units supported by the above supporting medium.

Furthermore, in the above-described measurement device, it is desirable that the dielectric block of the above measurement unit be immobilized to the above supporting medium, that a thin film layer and a sample-retaining mechanism of the measurement unit be unified so as to constitute a measurement chip, and that the measurement chip be formed such that it is exchangeable with respect to the above dielectric block.

When such a measurement chip is applied, it is desirable to establish a cassette for accommodating a multiple number of the measurement chips and a chip-supplying means for successively taking a measurement chip out of the cassette and supplying it in a state in which it is connected to the above dielectric block.

Otherwise, it may also be possible to unify the dielectric block of the measurement unit, the thin film layer and the sample-retaining mechanism, so as to constitute a measurement chip, and it may also be possible for this measurement chip to be formed such that it is exchangeable with respect to the above supporting medium.

When a measurement chip has such a structure, it is desirable to establish a cassette for accommodating a multiple number of measurement chips and a chip-supplying means for successively taking a measurement chip out of the cassette and supplying it in a state in which it is supported by the supporting medium.

The above optical system is desirably configured such that it makes a light beam enter the dielectric block in a state of convergent light or divergent light. Moreover, the above light-detecting means is desirably configured such that it detects the position of a dark line generated due to attenuated total reflection, which exists in the totally reflected light beam.

Furthermore, the above optical system is desirably configured such that it makes a light beam enter the above interface in a defocused state. In this case, the beam diameter of the light beam at the above interface in a direction wherein the above supporting medium moves is desirably ten times or greater the mechanical positioning precision of the above supporting medium.

Still further, the above-described measurement device is desirably configured such that the measurement unit is supported on the upper side of the above supporting medium, such that the above light source is placed so as to project the above light beam from a position above the above supporting medium to downwards, and such that the above optical system comprises a reflecting member for reflecting upwards the above light beam projected to downwards as described above and making it proceed towards the above interface.

Still further, the above-described measurement device is desirably configured such that the above measurement unit is supported on the upper side of the above supporting medium, such that the above optical system is constituted so as to make the above light beam enter the above interface from the downside thereof, and such that the above light-detecting means is placed in a position above the above supporting medium with a light-detecting plane thereof facing downwards, as well as comprising a reflecting member for reflecting upwards the totally reflected light beam at the above interface and making it proceed towards the above light-detecting means.

What is more, the above-described measurement device desirably comprises a temperature-controlling means for maintaining the temperature of the above measurement unit before and/or after being supported by the above supporting medium at a predetermined temperature.

Moreover, the above-described measurement device desirably comprises a means for stirring the sample stored in the sample-retaining mechanism of the measurement unit supported by the above supporting medium before detecting the state of attenuated total reflection as mentioned above.

Furthermore, in the above-described measurement device, it is desirable to establish in at least one of the multiple measurement units supported by the above supporting medium a standard solution-supplying means for supplying a standard solution having optical properties associated with the optical properties of the above sample, as well as a correcting means for correcting data regarding the above attenuated total reflection state of the sample based on the data regarding the above attenuated total reflection state of the above standard solution.

In such a case, if the sample is obtained by dissolving a test substance in a solvent, it is desirable that the above standard solution-supplying means be a means for supplying the above solvent as a standard solution.

Still further, the above measurement device desirably comprises: a mark for indicating individual recognition information; a reading means for reading the above mark from the measurement unit used in measurement; an inputting means for inputting sample information regarding the sample supplied to the measurement unit; a displaying means for displaying measurement results; and a controlling means connected to the above displaying means, inputting means and reading means, which stores the above individual recognition information and sample information of each measurement unit while associating them with each other, as well as making the above displaying means display the measurement results of the sample retained in a certain measurement unit while associating them with the above individual recognition information and sample information of each measurement unit.

When a substance interacting with a physiologically active substance is detected or measured using the above-described measurement device, a state of attenuated total reflection is detected in a sample contained in one of the above measurement units, and thereafter, the above supporting medium, optical system and light-detecting means are moved relative to one another, so that a state of attenuated total reflection is detected in a sample contained in another measurement unit. Thereafter, the above supporting medium, optical system and light-detecting means are again moved relative to one another, so that a state of attenuated total reflection is detected again the sample contained in the above one measurement unit, thereby completing the measurement.

The measurement chip used in the present invention is used for the surface plasmon resonance measurement device having a structure described herein, and comprises a dielectric block and a metal film formed on a face of the dielectric block, in which the dielectric block is formed as one block comprising the entirety of the entrance face and exit face of the light beam and a face on which the above metal film is formed, the above metal film is integrated with the above dielectric block.

A metal constituting the metal film is not particularly limited, as long as surface plasmon resonance is generated. Examples of a preferred metal may include free-electron metals such as gold, silver, copper, aluminum or platinum. Of these, thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably, the metal film has a functional group capable of immobilizing a physiologically active substance on the outermost surface of the substrate. The term "the outermost surface of the substrate" is used to mean "the surface, which is farthest from the substrate".

Examples of a preferred functional group may include —OH, —SH, —COOH, —$NR^1R^2$ (wherein each of $R^1$ and $R^2$ independently represents a hydrogen atom or lower alkyl group), —CHO, —$NR^3NR^1R^2$ (wherein each of $R^1$, $R^2$ and $R^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

Examples of the method of introducing such a functional group include a method which involves applying a polymer containing a precursor of such a functional group on a metal surface or metal film, and then generating the functional group from the precursor located on the outermost surface by chemical treatment.

In the measurement chip obtained as mentioned above, a physiologically active substance is covalently bound thereto via the above functional group, so that the physiologically active substance can be immobilized on the metal film.

A physiologically active substance immobilized on the surface for the measurement chip of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme, or nucleic acid, an amino group, thiol group or the like of the physiologically active substance is covalently bound to a functional group located on a metal surface, so that the physiologically active substance can be immobilized on the metal surface.

A measurement chip to which a physiologically active substance is immobilized as described above can be used to detect and/or measure a substance which interacts with the physiologically active substance.

Namely, the present invention provides a method for detecting or measuring a substance interacting with a physiologically active substance, which comprises steps of: using at least a measurement chip (cell), to the surface of which a physiologically active substance binds by covalent bonding; allowing a sample liquid containing a test substance to be measured to come into contact with the above cell; and after exchanging the liquid contained in a flow channel system, measuring a change in surface plasmon resonance in a state where the flow of the liquid has been stopped.

As a test substance, a sample containing a substance interacting with the aforementioned physiologically active substance can be used, for example.

The present invention will be described in detail by the following examples, but the present invention is not limited thereto.

EXAMPLES

The following experiment was carried out using a device shown in FIG. 22 of Japanese Patent Laid-Open No. 2001-330560 (hereinafter referred to as the surface plasmon resonance measurement device of the present invention) (shown in FIG. 1 of the present specification) and a dielectric block shown in FIG. 23 of Japanese Patent Laid-Open No. 2001-330560 (hereinafter referred to as the dielectric block of the present invention) (shown in FIG. 2 of the present specification).

Figure 1:
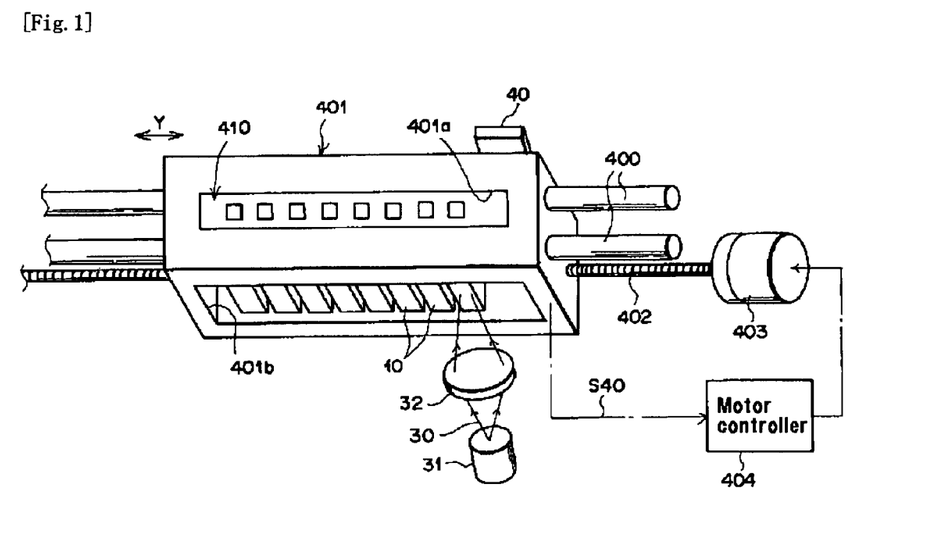
FIG. 1 shows a surface plasmon resonance measurement device used in the examples, wherein 10 indicates measurement unit, 30 indicates a light beam, 31 indicates laser light source, 32 indicates condenser lens, 40 indicates light detector, S40 indicates output signal, 400 indicates guide rod, 401 indicates slide block, 402 indicates precision screw, 403 indicates pulse motor, 404 indicates motor controller, and 410 indicates unit connector.

In the surface plasmon resonance measurement device shown in FIG. 1, a slide block 401 is used as a supporting medium for supporting measurement units, which is joined to two guide rods 400, 400 placed in parallel with each other while flexibly sliding in contact, and which also flexibly moves linearly along the two rods in the direction of an arrow Y in the figure. The slide block 401 is screwed together with a precision screw 402 placed in parallel with the above guide rods 400, 400, and the precision screw 402 is reciprocally rotated by a pulse motor 403 which constitutes a supporting medium-driving means together with the precision screw 402.

It is to be noted that the movement of the pulse motor 403 is controlled by a motor controller 404. This is to say, an output signal S 40 of a linear encoder (not shown in the figure), which is incorporated into the slide block 401 and detects the position of the slide block 401 in the longitudinal direction of the guide rods 400, 400, is inputted into the motor controller 404. The motor controller 404 controls the movement of the pulse motor 403 based on the signal S 40.

Moreover, below the guide rods 400, 400, there are established a laser light source 31 and a condenser 32 such that they sandwich from both sides the slide block 401 moving along the guide rods, and a photodetector 40. The condenser 32 condenses a light beam 30. In addition, the photodetector 40 is placed thereon.

In this embodiment, a stick-form unit connected body 410 obtained by connecting and fixing eight measurement units 10 is used as an example, and the measurement units 10 are mounted on the slide block 401 in a state in which eight units are arranged in a line.

Figure 2:
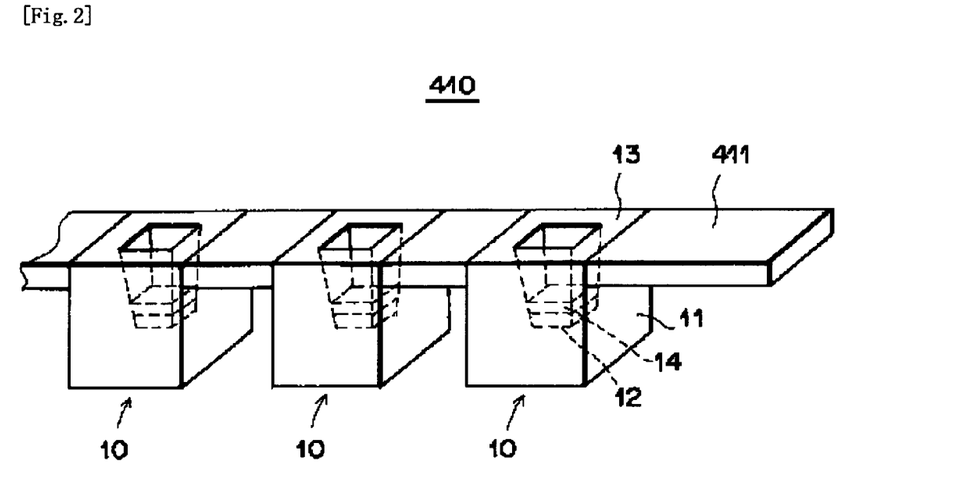
FIG. 2 shows the dielectric block used in the examples, wherein 10 indicates measurement unit, 11 indicates dielectric block, 12 indicates metal film, 13 indicates sample-retaining frame, 14 indicates sensing substance, 410 indicates unit connector, and 411 indicates connecting member.

FIG. 2 shows the structure of the unit connected body 410 in detail. As shown in the figure, the unit connected body 410 is obtained by connecting the eight measurement units 10 by a connecting member 411.

This measurement unit 10 is obtained by molding a dielectric block 11 and a sample-retaining frame 13 into one piece, for example, using transparent resin or the like. The measurement unit constitutes a measurement chip that is exchangeable with respect to a turntable. In order to make the measurement chip exchangeable, for example, the measurement unit 10 may be fitted into a through-hole that is formed in the turntable. In the present example, a sensing substance 14 is immobilized on a metal film 12.

Examples: Measurement in a State where the Flow of the Liquid has Been Stopped (1) Preparation of Dextran Assay Chip The dielectric block of the present invention onto which gold having a thickness of 50 nm had been evaporated as a metal film was treated with a Model-208 UV ozone cleaning system (TECHNOVISION INC.) for 30 minutes. Then, 5.0 mM solution of 11-hydroxy-1-undecanethiol in ethanol/water (80/20) was allowed to come into contact with the metal film, and surface treatment was carried out at 25° C. for 18 hours. Thereafter, the resultant product was washed with ethanol 5 times, with a mixed solvent consisting of ethanol and water 1 time, and then with water 5 times.

Subsequently, the surface coated with 11-hydroxy-1-undecanethiol was allowed to come into contact with a 10% by weight of epichlorohydrin solution (a solvent: a mixed solution of 0.4M sodium hydroxide and diethylene glycol dimethyl ether at a ratio of 1:1), and the reaction was allowed to proceed in a shaking incubator at 25° C. for 4 hours. The surface was washed twice with ethanol and 5 times with water.

Subsequently, 4.5 ml of 1M sodium hydroxide was added to 40.5 ml of 25% by weight of dextran (T500, Pharmacia) aqueous solution. The resulting solution was allowed to come into contact with the surface that had been treated with epichlorohydrin. The surface was then incubated in a shaking incubator at 25° C. for 20 hours. The surface was washed with water 10 times at 50° C. Subsequently, 3.5 g of bromoacetic acid was dissolved in 27 g of a 2M sodium hydroxide solution, the resulting mixture was allowed to come into contact with the dextran-treated surface, and the surface was then incubated in a shaking incubator at 28° C. for 16 hours. The surface was washed with water, and the procedure described above was repeated once.

(2) Preparation of a Chip having Protein A Immobilized Thereon:

After a solution in the dextran measurement chip prepared in the above (1) was removed, 70 μl of a mixed solution of 200 mM EDC (N-ethyl-N'-(3-dimethylaminopropyl)carbodiimide hydrochloride) and 50 mM NHS (N-hydroxysuccinimide) was added thereto, and the resultant was then allowed to stand for 10 minutes. After the mixed solution was removed, the chip was washed three times with 100 μl of water and then three times with 100 μl of acetate 5.0 buffer (BIAcore). The chip was mounted on the surface plasmon resonance measurement device of the present invention while containing 100 μl of acetate 5.0 buffer, the inside of the chip was replaced with a protein A solution (a solution of 50 μg/ml protein A (Nacalai Tesque Inc.) in acetate 5.0 buffer (BIAcore)), and the chip was allowed to stand for 30 minutes so that protein A was immobilized thereon. The inside of the chip was replaced with 1M ethanolamine solution and the chip was allowed to stand for 10 minutes. The inside of the chip was washed ten times with 100 μl of acetate 5.0 buffer. Change in the resonance signal resulting from protein A immobilization was 500 RU.

(3) Preparation of a Reference Chip:

After a solution in the dextran measurement chip prepared in (1) above was removed, 70 μl of a mixed solution of 200 mM EDC and 50 mM NHS was added thereto, and the resultant was then allowed to stand for 10 minutes. After the mixed solution was removed, the chip was washed three times with 100 μl of water and then three times with 100 μl of acetate 5.0 buffer. The inside of the chip was replaced with 1M ethanolamine solution and the chip was allowed to stand for 10 minutes. The inside of the chip was washed ten times with 100 μl of acetate 5.0 buffer.

(4) Preparation of a Flow Channel System:

A dielectric block was mounted on the chip having protein A immobilized thereon according to the present invention, and sealed with silicon rubber to prepare a cell having an inner volume of 15 μl. Two holes of a diameter of 1 mm were provided on the silicon rubber seal, and these two holes were connected with each other via a tefron tube having an inner diameter of 0.5 mm and an outer diameter of 1 mm to prepare a flow channel. Similarly, a cover and a flow channel were provided for the reference chip, these two chips were connected in series with each other, and the flow channel system was prepared. These two chips comprising the flow channel were mounted on the surface plasmon resonance measurement device of the present invention.

(5) Evaluation of Binding Capacity for Mouse IgG:

The flow channel system was filled with HBS-EP buffer (BIAcore). HBS-EP buffer was composed of 0.01 mol/l of HEPES (N-2-hydroxyethylpiperazine-N'-2-ethanesulfonic acid) (pH 7.4), 0.15 mol/l of NaCl, 0.003 mol/l of EDTA, and 0.005% by weight of Surfactant P20, Changes in the signal levels were assayed at intervals of 0.5 seconds by employing the signal level before liquid exchange as the baseline. The inside of the flow channel system was replaced with a mouse IgG solution (a solution of 10 μg/ml mouse IgG (purchased from Cosmo Bio Co., Ltd) in HBS-EP buffer) at 20 μl/sec. Such replacement was completed in 5 seconds.

The liquid flow was stopped 5 seconds after the initation of liquid exchange.

The data acquired 5 seconds to 2 minutes after the initation of liquid exchange were used, initial values, $ka=1\times10^5$ $(M^{-1}s^{-1})$, $kd=1\times10^{-3}$ $(s^{-1})$, Rmax=500 (RU), $D=1\times10^{-7}$ $(cm^2\ s^{-1})$, and $C=6.7\times10^{-8}$ (M), were assigned, and ka, kd, Rmax, and D values were converted using the Solver functions (Excel 2000, Microsoft). The curve exhibiting the smallest errors by the method of least squares from the curve indicating the measured value was determined by the nonlinear regression method. The results are shown in FIG. 4. This demonstrates that the curve indicating the measured value is substantially consistent with the curve indicating the calculated value.

Comparative Example: Measurement in a State where Liquid is Flowing

The following experiment was carried out using the BIAcore 3000 (BIAcore). The sensorchip CM-5 was mounted by a conventional method, and priming was performed using HBS-EP buffer. A buffer and various solutions were allowed to flow through the flow cell 2 at a flow rate of 10 μl/min to perform the experiment. After the mixed solution of 200 mM EDC and 50 mM NHS was allowed to flow for 7 minutes, the HBS-EP buffer was allowed to flow to wash the cell. Subsequently, a protein A solution (Protein A, Nacalai Tesque, Inc.) was dissolved in Acetate 5.0 (BIAcore) to 10 μg/ml, and the resulting solution was allowed to flow therethrough for 1 minute so as to immobilize protein A. After the protein A solution was washed with the HBS-EP buffer, a 1M ethanolamine solution was allowed to flow for 7 minutes. The ethanolamine solution was washed with the HBS-EP buffer. Changes in resonance signals resulting from immobilization of protein A were 300 RU.

A buffer and various solutions were allowed to flow through the flow cell 1 at a flow rate of 10 μl/min to perform the experiment. After the mixed solution of 200 mM EDC and 50 mM NHS was allowed to flow for 7 minutes, the HBS-EP buffer was allowed to flow to wash the cell. A 1M ethanolamine solution was allowed to flow for 7 minutes. The ethanolamine solution was washed with the HBS-EP buffer.

A buffer and various solutions were allowed to flow through the flow cells 1 and 2 at a flow rate of 20 μl/min to perform the experiment. A mouse IgG solution (a solution of mouse IgG (purchased from Cosmo Bio) dissolved in HBS- EP buffer to 10 μg/ml) was injected using "kinject" command, and binding and dissociation signals were measured 5 minutes.

The measured signals were subjected to fitting using an analytical software, BIA evaluation 3.1 (BIAcore), in the 1:1 (Langmuir) binding mode, so as to determine ka, kd, and Rmax.

Parameters obtained in Examples and Comparative Example are shown in Table 1, ka and kd values obtained in Examples were found to be similar to values obtained in Comparative Example. Also, the dissociation constant with satisfactory baseline fluctuations could be determined in the same manner as with the ideal conditions.

TABLE 1

|  | ka | kd | Rmax | D | Noise (RU) | Baseline fluctuation (RU/min) | Amount of analyte solution used (μl) |
| --- | --- | --- | --- | --- | --- | --- | --- |
| Example | $3.5 \times 10^5$ | $9.0 \times 10^{-4}$ | 640 | $4.1 \times 10^{-8}$ | <1 | <1 | 100 |
| Comparative Example | $2.6 \times 10^5$ | $7.8 \times 10^{-4}$ | 425 | — | 6 | 5 | 140 |

INDUSTRIALLY APPLICABILITY

According to the present invention, the dissociation constant of an analyte molecule immobilized on a metal surface and a molecule that interacts therewith can be determined by surface plasmon resonance (SPR) analysis by a method for measuring changes in surface plasmon resonance signals in a state where the flow of the liquid has been stopped, after the liquid contained in the above flow channel system of the plasmon resonance measurement device has been exchanged, which can yield highly reliable results of measurement with a low noise level (i.e., a noise width of a control chip) and small baseline fluctuations (i.e., signal changes of a control chip).

The invention claimed is:

1. A method for determining a dissociation constant of an analyte molecule immobilized on a metal surface and a molecule that interacts therewith, wherein changes in surface plasmon resonance signals are measured by using a surface plasmon resonance measurement device comprising a flow channel system having a cell formed on a metal film and a light-detecting means for detecting the state of surface plasmon resonance by measuring the intensity of a light beam totally reflected on the metal film; wherein a change in surface plasmon resonance signals is measured in a state where the flow of the liquid has been stopped, after the liquid contained in the above flow channel system has been exchanged; and wherein the dissociation constant is determined based on the results of measurement of signal changes.

2. The method according to claim 1, wherein an adsorption rate coefficient (ka) and a dissociation rate coefficient (kd) are determined based on the results of measurement of changes in surface plasmon resonance signals, and a dissociation constant (KD) is determined using an equation represented by KD=kd/ka based on the determined adsorption rate coefficient (ka) and the dissociation rate coefficient (kd).

3. The method according to claim 1, wherein an adsorption rate coefficient (ka) and a dissociation rate coefficient (kd) are determined based on the results of measurement of changes in surface plasmon resonance signals by using the following equations (1), (2), and (3):

$$d\theta/dt = ka \times c_s \times (1-\theta) - kd \times \theta \quad (1)$$

wherein θ represents an adsorption ratio (=amount of adsorption/amount of saturated adsorption); ka represents an adsorption rate coefficient; kd represents a dissociation rate coefficient; and $c_s$ represents the concentration of the analyte molecule that exists near the metal surface;

$$\partial c/\partial t = D \times \partial^2 c/\partial x^2 \quad (2)$$

wherein x represents a distance from a metal surface; D represents a diffusion coefficient of the analyte molecule; and c represents the concentration of the analyte molecule, provided that when x is 0, c is $c_s$; and $$\theta = R/R\text{max} \quad (3)$$

wherein θ represents an adsorption ratio (=amount of adsorption/amount of saturated adsorption); R represents a surface plasmon signal; and Rmax represents a signal resulting when an analyte molecule is saturatedly adsorbed.

4. The method according to claim 1, wherein the dissociation constant is determined while making corrections based on the supposition that the time required for the liquid exchange is an adsorption phenomenon under ideal conditions.

5. The method according to claim 1, wherein the dissociation constant is determined by using nonlinear regression analysis.

6. The method according to claim 1, which comprises using a surface plasmon resonance measurement device comprising a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, a flow channel system comprising a cell formed on the above metal film, and a light-detecting means for detecting the state of surface plasmon resonance by measuring the intensity of the light beam totally reflected at the above interface.

7. The method according to claim 1 wherein the liquid contained in the above flow channel system is exchanged from a reference liquid containing no test substance to be measured to a sample liquid containing a test substance to be measured, and thereafter, the change in surface plasmon resonance is measured in a state where the flow of the sample liquid has been stopped.

8. The method according to claim 1 wherein a reference cell, to which a physiologically active substance interacting with a test substance does not bind, is connected in series with a detection cell, to which the physiologically active substance interacting with the test substance binds, the connected cells are placed in the flow channel system, and the liquid is then fed through the reference cell and the detection cell.

9. The method according to claim 8 wherein the ratio (Ve/Vs) of the amount of the liquid exchanged (Ve ml) in a single measurement to the volume of the above cell (Vs ml) is between 1 and 100.

10. The method according to claim 9 wherein the ratio (Ve/Vs) is between 1 and 50.

11. The method according to claim 1 wherein the time required for the exchange of the liquid contained in the above flow channel system is between 0.01 second and 100 seconds.

* * * * *